United States Patent [19]
Magnani et al.

[11] Patent Number: 6,139,836
[45] Date of Patent: Oct. 31, 2000

[54] METHOD OF ENCAPSULATING BIOLOGICALLY ACTIVE AGENTS WITHIN ERYTHROCYTES, AND APPARATUS THEREFOR

[75] Inventors: Mauro Magnani, Urbino; Ivo Panzani, Mirandola; Leonardo Bigi, Mirandola; Andrea Zanella, Mirandola, all of Italy

[73] Assignee: Dideco, S.p.A., Mirandola, Italy

[21] Appl. No.: 09/071,005

[22] Filed: May 1, 1998

[30]     Foreign Application Priority Data

May 5, 1997 [EP] European Pat. Off. ............. 97830211

[51] Int. Cl.[7] .................................................. A01N 63/00
[52] U.S. Cl. .................... 424/93.73; 424/93.1; 424/93.3; 424/93.7; 435/2
[58] Field of Search ............................... 435/2; 424/93.1, 424/93.3, 93.7, 93.73

[56]                References Cited

U.S. PATENT DOCUMENTS

| | | | |
|---|---|---|---|
| 4,224,313 | 9/1980 | Zimmermann et al. | 424/94 |
| 4,269,826 | 5/1981 | Zimmermann et al. | 424/101 |
| 4,289,756 | 9/1981 | Zimmermann et al. | 424/101 |
| 4,327,710 | 5/1982 | DeLoach et al. | 128/1 R |
| 4,420,559 | 12/1983 | Zimmermann | 435/99 |
| 4,478,824 | 10/1984 | Franco et al. | 424/101 |
| 4,652,449 | 3/1987 | Ropars et al. | 424/101 |
| 4,931,276 | 6/1990 | Franco et al. | 424/533 |
| 5,589,389 | 12/1996 | Pages et al. | 435/306.1 |

FOREIGN PATENT DOCUMENTS

| | | |
|---|---|---|
| 0 517 986 A1 | 12/1992 | European Pat. Off. . |
| 2 678 512 | 1/1983 | France . |
| 2 529 463 | 1/1984 | France . |
| 23 26 161 C2 | 12/1974 | Germany . |
| 23 26 244 C3 | 12/1974 | Germany . |

OTHER PUBLICATIONS

Magnani et al., "Erythrocyte Engineering for Drug Delivery and Targeting," *Biotechnol. Appl. Biochem.*, 28(1):1–6 (Aug. 1998).

Chiarantini, L., et al., "Modulated Red Blood Cell Survival by Membrane Protein Clustering," *Molecular and Cellular Biochemistry*, 144:53–59, 1995.

Franco, R., et al., "Effect of Inositol Hexaphosphate on the Transient Behavior o Red Cells Following a DMSO–Induced Osmotic Pulse," *Journal of Cellular Physiology*, 129:221–229 (1986).

Franco, R., et al., "Incorporation of Inositol Hexaphosphate into Red Blood Cells Mediated by Dimethyl Sulfoxide," *Life Sciences*, 32:2763–2768 (1983).

Franco, R., et al., "Preparation of Low–Affinity Red Cells with Dimethylsulfoxide–Mediated Inositol Hexaphosphate Incorporation: Hemoglobin and ATP Recovery Using a Continuous–Flow Method," *American Journal of Hematology*, 17:393–400 (1984).

Heubusch, P., et al., "The Osmotic Response of Human Erythrocytes and the Membrane Cytoskeleton," *Journal of Cellular Physiology*, 122:266–272 (1985).

Jain, S., et al., "Magnetically Responsive Diclofenac Sodium–Loaded Erythrocytes: Preparation and In Vitro Characterization," *Journal of Microencapsulation*, 11:141–151 (1994).

(List continued on next page.)

*Primary Examiner*—Dwayne C. Jones
*Assistant Examiner*—C. Delacroix-Muirheid
*Attorney, Agent, or Firm*—Popovich & Wiles, P.A.

[57]                ABSTRACT

A method and apparatus for the encapsulation of biologically active agents in red blood cells (RBCS) is disclosed. The method is characterized in that lysed and partially lysed RBCs are concentrated prior to the introduction of the biologically active agent. The resultant carrier RBCs are stable for an extended period of time under physiological conditions and can be used for the systemic or targeted delivery of therapeutically effective amounts of one or more biologically active agents to a patient.

24 Claims, 2 Drawing Sheets

OTHER PUBLICATIONS

Magnani, M., et al., "Targeting Antiretroviral Nucleoside Analogues in Phosphorylated Form to Macrophages: In Vitro and In Vivo Studies," *Proc. Natl. Acad. Sci. USA*, 89:6477–6481 (1992).

Magnani, M., et al., "Targeting Dexamethasone to Macrophages," *Drug Delivery*, 2:151–155 (1995).

Rechsteiner, M., "Uptake of Proteins by Red Blood Cells," *Exptl. Cell Res.*, 93:487–492 (1975).

Ropars, C., et al., "Resealed Red Blood Cells as a New Blood Transfusion Product," *Biblthca haemat.*, 51:82–91 (Karger, Basil 1985).

Talwar, N., et al., "Erythrocytes as Carriers of Primaquine–Preparation: Characterization and Evaluation," *Journal of Controlled Release*, 20:133–141 (1992).

European Search Report for EP 97830211, dated Oct. 20, 1997, 4 pages.

METHOD OF ENCAPSULATING BIOLOGICALLY ACTIVE AGENTS WITHIN ERYTHROCYTES, AND APPARATUS THEREFOR

FIELD OF THE INVENTION

The present invention relates to a method for the incorporation of biologically active agents into red blood cells.

BACKGROUND OF THE INVENTION

Much effort has been recently focused on the development of procedures for the targeted delivery of pharmaceutical agents to specific sites in a patient. It is known that drug efficacy can be increased when the appropriate target site is efficiently reached, and drug toxicity can be reduced when the total amount of drug administered is minimized. The interest in drug delivery systems applies both to conventional agents, many of which are relatively simple organic molecules, as well as to more complex agents such as oligopeptides, proteins and nucleic acids, etc. One area of recent interest relates to the use of red blood cells (hereafter erythrocytes and RBCs) to deliver therapeutic dosages of drugs to a target site in a patient. Erythrocytes can be "loaded" with biologically active agents by a process in which the cell membranes of the erythrocytes are lysed and one or more agents is added to the erythrocytes, followed by resealing of the cell membranes. Such "loaded" or "carrier" erythrocytes offer a number of advantages as drug delivery and targeting systems because they are biodegradable, can be maintained in the circulatory system for long periods of time, and can be targeted to selected cells such as, for example, macrophages. However, although the use of erythrocytes as drug delivery systems has been investigated by many, the method has not yet developed to the point where it can be applied routinely in a clinical setting.

Processes for the preparation of a suspension of loaded cells in a physiological solution are disclosed in German Patent No. 23 26 244 and in German published Patent Application Nos. (OS) 23 26 161 and 24 95 119, in which the erythrocyte cell membranes are lysed by either osmotic pressure or an electrical field, respectively.

U.S. Pat. No. 4,224,313, (Zimmermann et al.), discloses a method for preparing a mass of loaded cells suspended in a solution by increasing the permeability of the cell membranes via externally induced osmotic pressure or an electric field, or both. The material to be loaded includes a pharmaceutical agent having a capability, when incorporated in a cell, of prematurely destroying cell membranes, and a stabilizing agent capable of inhibiting the reaction of the pharmaceutical agent with the cell membranes.

U.S. Pat. No. 4,269,826, (Zimmermann et al.), discloses a method for incorporating magnetic substances within loaded cells that can be localized to a specific part of a living body by application of an external magnetic field.

U.S. Pat. No. 4,289,756, (Zimmermann et al.), discloses a method for preferentially accumulating loaded cells within the spleen and liver of a living body.

U.S. Pat. No. 4,478,824, (Franco et al.), discloses a method for incorporating substances into erythrocytes by changing the internal osmotic pressure of RBCs by the action of chemical agents, such as DMSO and glycerol, that can pass through the cell membrane and enter cells by diffusion.

U.S. Pat. No. 4,652,449, (Ropars et al.), discloses a method and apparatus for incorporating materials into erythrocytes using osmotic pressure. The method and apparatus have been used and tested only with large volumes of blood, which limits many applications to the use of homologous blood, i.e., blood pooled from many individual sources. U.S. Pat. No. 4,931,276, (Franco et al.), discloses a method for the encapsulation of non-ionic agents within erythrocytes. The method is of limited effectiveness where the desired agent to be incorporated is not anionic, or is anionic or polyanionic but is not present in the near-isotonic aqueous medium in sufficient concentration to cause needed increases in cell permeability without cell destruction.

Heubsch et al., J. Cell. Physiol., 122:266–272 (1985), demonstrate that cytoskeletal detachment occurs in osmotically swollen cells and that with extreme changes in size, the bilayer membrane is released from a deformational constraint which is present under normal conditions.

Reviews of methods of incorporating substances into cells are presented by Franco et al. in Life Science 32:2763–2768 (1983), Am. J. Hematol. 17:393–400 (1984), and J. Cell. Physiol. 129:221–229 (1986).

SUMMARY OF THE INVENTION

Despite the extensive work in the field of the present invention, there is still no method known in the prior art which provides for the introduction of one or more biologically active agents into RBCs at acceptable physiological concentrations without the dilution or loss of the endogenous contents of the erythrocytes. It is a primary object of the present invention to provide a method which fulfills this need. That is, the method of the invention provides for the introduction of one or more biologically active agents (i.e., drugs) into erythrocytes at desirable physiological concentrations without the dilution or loss of a substantial portion of the cellular contents, which undesirably decreases the integrity, viability and longevity of carrier RBCs.

More particularly, it is an object of the present invention to provide such a method using a small volume of blood so that autologous carrier RBCs may be prepared for individual patients, and without the need for cooling of the blood at any stage of the process.

It is a further object of the invention to provide carrier (i.e., drug-loaded) erythrocytes that possess the ability to persist, and to release biologically active agents, under mammalian physiological conditions for a longer period of time than previously described carrier RBCs. Carrier RBCs made according to the present invention release their encapsulated biologically active agent(s) by diffusion out of the RBCs or by active transport across the erythrocyte cell membrane.

It is a further object of the present invention to provide an apparatus by which the method of the invention can be efficiently and reproducibly carried out. More particularly, it is an object of the present invention to provide an apparatus by which autologous carrier RBCs may be prepared from a small volume of blood from an individual patient in a matter of hours.

Thus, the invention relates to the incorporation of a wide variety of therapeutically useful biologically active agents into mammalian erythrocytes which could not previously be accomplished without unacceptable dilution of the endogenous erythrocyte contents and/or the agent(s) to be incorporated within the erythrocytes. More particularly, the method of the present invention makes possible the introduction or incorporation of various agents, including polypeptides, into erythrocytes. These and other biologically active agents may be encapsulated, either alone or in combination with other such agents, within erythrocytes that thus become carrier erythrocytes for the agent(s). The carrier erythrocytes are used to achieve a desired slow continuous delivery of the encapsulated biologically active agent(s) when the carrier erythrocytes are later introduced into a mammal. Moreover, the invention provides for the rapid preparation of such carrier erythrocytes from relatively small samples of blood and thus allows for the preparation of autologous carrier erythrocytes from an individual patient. The method of the invention has particular utility when used with an apparatus as described herein.

The above objects are achieved, in accordance with the present invention, in a method of introducing at least one desired agent into mammalian red blood cells (RBCs), which comprises concentrating lysed or partially lysed erythrocyte material before adding one or more biologically active agents to be encapsulated and which significantly improves the encapsulation yield. Concentration of the lysed or partially lysed erythrocyte material can be achieved by a variety of means, including hemofiltration, which uses a high flux hemodialyzer such as a hollow fiber dialyzer with a high ultrafiltration rate. In a preferred embodiment, a disposable hemofilter cartridge is used as the concentrating means in the method of the invention.

DETAILED DESCRIPTION OF THE PREFERRED EMBODIMENTS

Figure 1:
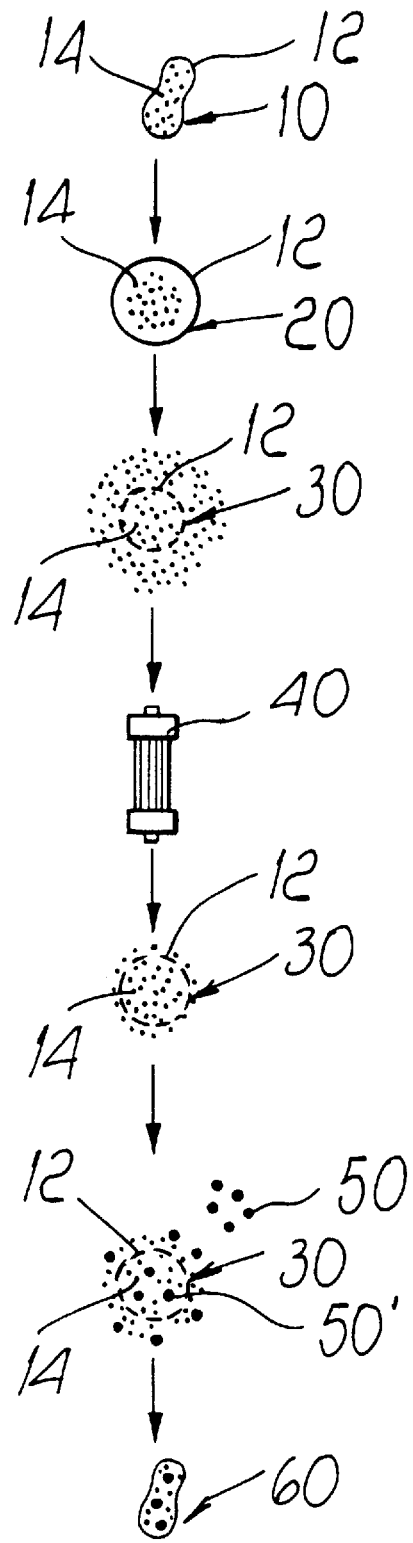
FIG. 1 schematically shows one preferred embodiment of the method of the invention.

The method of the present invention provides for the introduction of at least one desired agent into mammalian red blood cells. The method involves concentrating lysed or partially lysed erythrocyte material before adding one or more biologically active agents to be encapsulated and has been found to significantly improve the encapsulation yield. As used herein, "encapsulation yield" refers to the fraction of a biologically active agent that is encapsulated within carrier RBCs, and is usually expressed as the percentage of encapsulated agent relative to the total amount of agent added during the encapsulation process. The erythrocyte material can be concentrated by a variety of means, including hemofiltration, which uses a high flux hemodialyzer such as a hollow fiber dialyzer with a high ultrafiltration rate. In a preferred embodiment, a disposable hemofilter cartridge is used as the concentrating means in the method of the invention.

As used herein, the term "carrier RBCs" refers to erythrocytes which encapsulate one or more biologically active agents. In some instances, carrier RBCs containing an added biologically active agent are described herein with respect to the specific agent. For example, "d-21P carrier RBCs" refers to erythrocytes that have been lysed, loaded with the agent dexamethasone-21-phosphate (d-21P), and release dexamethasone. Carrier RBCs for a variety of such agents, either alone or in combination, can be prepared by the method of the invention.

As used herein, the term "biologically active agents" refers to materials capable of being encapsulated using the methods of the present invention. These include, but are not limited to, peptides, oligopeptides, polypeptides, proteins, hormones, corticosteroids, glucocorticoids, non-steroidal anti-inflammatory agents, glutathione, cytokines, toxins, oligonucleotides and other nucleic acids, and nucleoside analogs that are well known as useful therapeutic agents. These include 6-mercaptopurine (6-MP) or azathiopurine and fludarabine phosphate, which are commonly used as immunosuppressants and inhibitors of malignant cell growth, and phosphorylated azidothymidine (AZT), dideoxycytosine (ddC) and dideoxyinosine (ddI), which are useful as antiviral agents, particularly in the treatment of AIDS. Carrier RBCs made by the method of the present invention have the desirable attribute of enhanced integrity, viability and longevity under physiological conditions.

The following abbreviations are used throughout:

BS$^3$ bissulfosuccinimidilsuberate
d-21P dexamethasone-21-phosphate
PIGPA Phosphate-Inosine-Glucose-Pyruvate-Adenine
RBCs red blood cell(s), erythrocytes
CPD Sodium citrate dihydrate-Citric acid monohydrate-Sodium phosphate monobasic bihydrate-Glucose
PBS(1)phosphate buffered saline
[1]Physiological saline (NaCl 0.9% w/v) may be substituted for PBS.

In one embodiment, the method of the present invention comprises collecting erythrocytes from an individual patient, concentrating the erythrocytes, washing the erythrocytes with a first solution of a physiological saline, washing the erythrocytes with a second, hypotonic solution consisting of 6 volumes of a physiological saline solution and 4 volumes of distilled sterile $H_2O$, diluting the erythrocytes with a solution consisting of 6 volumes of phosphate buffered saline (PBS) and 8 volumes of distilled sterile $H_2O$, concentrating of the erythrocytes in a hemofilter cartridge, adding the biologically active agent or agents to be encapsulated, sealing the erythrocytes by addition of a sealing solution, incubating the resulting erythrocytes at about 37° C. for about 30 minutes, and washing the erythrocytes with a physiological saline solution. The sealing solution is preferably Phosphate-Inosine-Glucose-Pyruvate-Adenine (PIGPA), which comprises about 33 mM $NaH_2PO_4$; about 1.606 M KCl; about 0.194 M NaCl; about 0.1 M inosine; about 5 mM adenine; about 20 mM ATP; about 0.1 M glucose; about 0.1 M pyruvate; and about 4 mM $MgCl_2$. In a preferred embodiment, about 5 ml of the PIGPA solution is used for sealing a volume of about 70–90 ml of lysed erythrocytes.

In order to prevent the erythrocytes from coagulating during the process, they may be optionally contacted with an anticoagulant during or subsequent to the collection step. One preferred anticoagulant solution, referred to herein as CPD solution comprises 26.3 g sodium citrate dihydrate, 3.3 g citric acid monohydrate, 2.5 g sodium phosphate monobasic dihydrate, and 23.2 g glucose in 1 liter of sterile water.

More particularly, the method of the present invention involves separating erythrocytes from other blood cells and components, suspending the erythrocytes in a first hypotonic solution at a concentration of about 0.04 to about 0.05 ml of erythrocytes for each ml of the first solution (the volume and osmolality of the first solution being known or determined), lysing the erythrocytes by suspending them in a second hypotonic solution (having an osmolality that is about 30 to about 60 mOsm less than that of the first solution) to obtain a lysate, adjusting the concentration of the lysate so that its volume is about 0.1 to about 0.067 that of the volume of the first solution, adding a biologically active agent to be encapsulated to the lysate, and sealing the lysed RBCs by adding a concentrated saline solution to the lysate to adjust he osmolality of the lysate to a range of about 1.9 to about 2.1 times that of the first solution.

A preferred embodiment of the method of the invention is shown schematically in FIG. 1. In FIG. 1, erythrocytes 10 are represented as a membrane 12 containing numerous small filled circles. The small filled circles are intended to represent biological molecules 14 endogenous to unlysed RBCs. After the first hypotonic dilution, it is seen that the erythrocytes 10 become swollen (schematically represented as 20). The swollen erythrocytes 20 are exposed to a second hypotonic dilution, which causes them to become fully or partially lysed. The lysed or partially lysed erythrocytes 30 both enclose, and are surrounded by, biological molecules 14 endogenous to unlysed RBCs. In the next step, the lysed or partially lysed erythrocytes 30 are then concentrated in a hemofilter 40. The resulting lysed or partially lysed erythrocytes 30 are contacted with biologically active agents 50 represented by the large filled circles. In so doing, some of the biologically active agents become encapsulated within the erythrocytes. The encapsulated biologically active agents are schematically represented as 50. The erythrocytes, now containing biologically active agents, are then exposed to a concentrated saline solution. The exposure causes the cell membranes 12 to seal, thereby capturing and encapsulating biologically active agents 50 within the cell. The resulting, so-called carrier RBC or carrier erythrocyte 60 is then washed.

Figure 2:
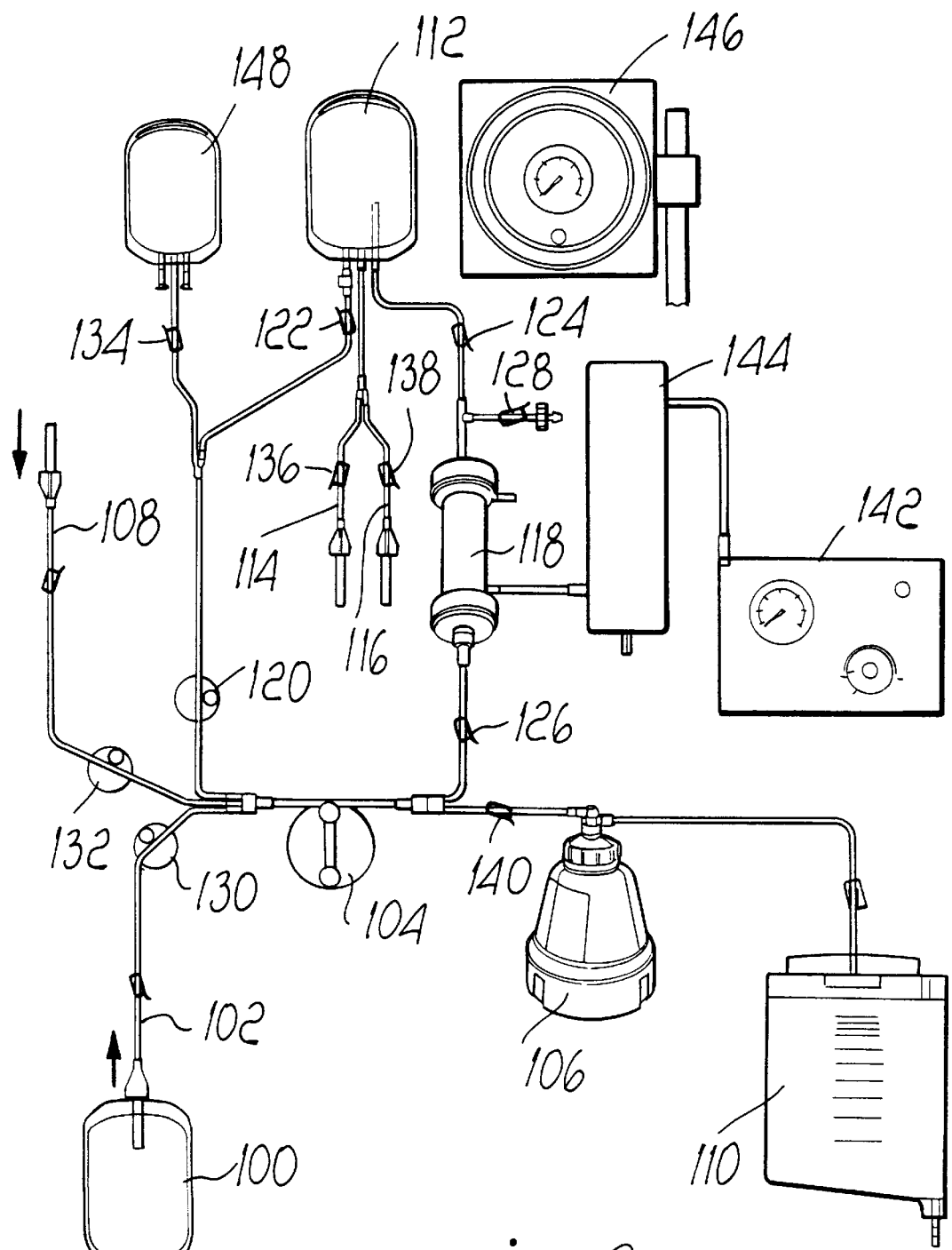
FIG. 2 is a schematic representation of an apparatus useful for carrying out the method of the present invention.

One embodiment of the apparatus for carrying out the method described above is shown schematically in FIG. 2. In FIG. 2, a bag 100 preferably containing at least 50 ml of blood (collected from a patient) is connected to a blood feed line 102. The blood is transferred, by a pump 104 to a separation bowl 106, preferably rotating at about 5600 rpm. Erythrocytes contained within the bowl 106 are washed by a physiological saline solution (NaCl 0.6%) provided by a physiological saline feed line 108. The physiological saline is preferably supplied at a rate of about 150 ml/min. The washing procedure separates plasma and the other blood cells which are transferred to a waste collection bag 110. After washing, the erythrocytes are pumped from the separation bowl 106 to a transfer bag 112. About 400 ml of a first hypotonic solution (6 volumes physiological saline and 4.5 volumes distilled water) are added to the transfer bag 112 via a first hypotonic solution feed line 114 and mixed with the erythrocytes. The resulting suspension is then maintained at room temperature for about 5–10 minutes under gentle agitation. At this point the erythrocytes have become swollen (reference numeral 20 of FIG. 1), but they have not yet been lysed. A second hypotonic solution is then introduced into the transfer bag 112 via a second hypotonic solution feed line 116. The second hypotonic solution is preferably about 200 ml of a solution having 6 volumes physiological saline and 8 volumes distilled water. It is at this stage that hemolysis of the erythrocytes occurs. After about 15 minutes at room temperature, the resulting lysate is pumped through the hemofilter 1 18. During the filtration process, clamps 120, 122, 124 and 126 are open, and clamps 128, 130, 132, 134, 136, 138 and 140 are closed. To enhance the filtration process, an optional vacuum pump 142, drawing a vacuum of about 100 to about 150 mmHg, may be employed. Hemolysate is collected in an ultrafiltrate reservoir 144 until the volume of the filtrate is in the range of about 170 to 190 ml. Once the desired volume has been achieved, the concentrated erythrocytes are collected in the transfer bag 112. This is accomplished by closing clamp 124 and opening clamp 128. The biologically active substance is then introduced into the transfer bag 112, at which point it contacts and becomes encapsulated by the concentrated, lysed erythrocytes. After about 10 to 15 minutes of gentle agitation, 5 ml of PIGPA sealing solution is added to the transfer bag 112, and the bag is placed into a heater 146 for about 30 min at about 37° C. to incubate the erythrocytes. Upon completion of the desired heating time, the transfer bag 112, now containing resealed erythrocytes, is reconnected, and the erythrocytes are pumped back into the separation bowl 106. Once in the bowl, the erythrocytes are washed with about 2 liters of physiological saline (supplied at about 150 to 200 ml/min) while the bowl is rotated at about 5600 rpm. Finally, the washed, loaded erythrocytes are transferred into the loaded erythrocyte bag 148. This is achieved by closing clamp 122 and opening clamp 134 while pumping the erythrocytes from the bowl at a rate of about 150 ml/min. The erythrocyte suspension is now ready for gravity infusion into a patient. As noted above, the patient may be either the patient who supplied the processed blood or another.

The erythrocytes encapsulating at least one biologically active agent may also be treated with a targeting agent so that the treated erythrocytes are preferentially directed to a specific tissue or cell type. For example, in the case in which drug-loaded erythrocytes are to be processed for the induction of their rapid recognition by macrophages, prior to pumping the loaded erythrocytes into bag 148, they are subjected to an additional washing step with a physiological saline solution containing 1 mM $ZnCl_2$. Once contacted with $ZnCl_2$, the erythrocytes are transferred to the transfer bag 112 where they are contacted with $BS^3$ (1–1.5 mM final concentration). After about 15 minutes, the erythrocytes are again washed in the rotating separation element 106 using approximately 1 liter of physiological saline. They are then transferred to the loaded erythrocyte bag 148, from where they may be infused into a patient.

If the loaded erythrocytes are to be stored longer than about 12 to 24 hours prior to infusion, the final collecting bag should contain a preservative. One preferred preservative is the CPD solution described above. Thus, approximately 10 ml of CPD solution may be provided in the final collecting bag.

The embodiment shown in FIG. 2 is particularly preferred for the preparation of autologous carrier RBCs from a small volume (less than 100 ml) of blood from an individual patient at room temperatures, i.e., without requiring any heating or cooling of whole blood or any of the cellular or molecular components of blood. As used herein, "an individual patient" is not limited to humans and refers to any mammal to which carrier RBCs are desired to be administered. Furthermore, as used herein, "autologous carrier RBCs" refers to erythrocytes isolated from a given individual patient that have been modified in vitro to encapsulate one or more biologically active agent(s) and which are intended to be reintroduced into the individual patient from which the erythrocytes were originally isolated. There are many advantages to the use of autologous carrier RBCs to treat individual patients and, in particular, undesirable immune responses that might, for example, shorten the in vivo lifetime of the carrier RBCs are avoided by the use of erythrocytes derived from the individual patient.

Due to the higher concentration of added active agents in the carrier erythrocytes made by the method of the present invention, the carrier RBCs are not as rapidly depleted of such agents as those made by previously known methods. Moreover, due to the higher proportion of endogenous biological molecules that are released from lysed RBCs but which, by the method of the present invention, are nevertheless re-introduced at a high concentration into the carrier RBCs, carrier erythrocytes made by the method of the present invention are not depleted for endogenous molecules needed for their long-term maintenance, as are carrier RBCs made by previously known methods. As a consequence, the carrier RBCs of the present invention possess an ability to persist and release active agents under physiological conditions for a longer period of time than previously described carrier RBCs.

The carrier RBCs of the present invention are administered via injection into a mammal in order to provide the encapsulated biologically active agent(s) thereof to the mammal without further manipulation for an extended period of time. If systematic delivery is required, then the carrier RBCs are injected into the circulatory system of the mammal. Targeted delivery of the carrier RBCs is achieved by intramuscular injection in the region of interest.

In another embodiment of the invention, a "predrug" (i.e., precursor to a biologically active agent) is incorporated into carrier RBCs that are then injected into a mammal. For some predrugs, endogenous activating agents present in the blood of the mammal will convert the predrug into a biologically active agent at a slow but steady rate. As an example, dexamethasone-21-phosphate (d-21P) may be encapsulated in carrier RBCs and, when the loaded RBCs are introduced into the circulatory system of a mammal, the d-21P is slowly converted into the chemotherapeutic drug dexamethasone. Because dexamethasone can cross the cell membrane of the carrier erythrocytes, (while d-21P cannot), this process assures that the mammal is provided with a constant level of the biologically active agent, (in this case dexamethasone), over some period of time. Alternatively, for predrugs for which no endogenous activating agents exist, an activating agent can be added to the blood of the mammal at a desired point in time. The activating agent enters the loaded erythrocytes and activates the predrug by, e.g., reacting with the predrug to form a biologically active agent, or by catalyzing a chemical reaction that converts the predrug. In a related embodiment, the activating agent may be encapsulated into erythrocytes which are introduced into a patient followed by the subsequent introduction of the predrug to the patient.

Carrier RBCs made by the method of the present invention are used to deliver a therapeutically effective amount of the biologically active agent(s) encapsulated therein to an individual patient. The term "therapeutically effective amount", for the purposes of the present invention, refers to the amount(s) of biologically active agent(s) effective to achieve an intended purpose. While individual needs vary, determination of optimal ranges for therapeutically effective amounts of such agents is within the skill of the art. Generally, the dosage required to provide a therapeutically effective amount of the composition can be determined by one of ordinary skill in the art and will vary depending on the age, health, physical condition, weight, extent of disease of the individual, frequency of treatment and the nature and scope of the desired effect. Where appropriate, a therapeutically effective amount can be delivered via multiple administrations of carrier RBCs over an appropriate period of time.

The carrier RBCs of the invention can be included in a pharmaceutical composition that also comprises additional substances, such as conventional excipients, i.e., pharmaceutically acceptable organic or inorganic carrier substances suitable for administration to a mammal via injection which do not deleteriously react with the active compound. Suitable pharmaceutically acceptable carriers include, but are not limited to, water, salt solutions, polyethylene glycols, gelatin, etc. Additionally or alternatively, pharmaceutical preparations comprising the carrier RBCs of the invention can further comprise auxiliary agents, e.g., lubricants, preservatives, stabilizers, wetting agents, emulsifiers, salts for influencing osmotic pressure, buffers, and the like, which do not deleteriously react with the active compounds. Pharmaceutical compositions comprising the carrier RBCs of the invention may also optionally contain stabilizing agents.

One example of a polypeptide that is suitable for use with the present invention is ubiquitin, a polypeptide having a molecular weight of 8,600 Daltons. Ubiquitin is known to mark proteins for subsequent proteolytic degradation. Typically, the percentage of polypeptide that can be encapsulated into carrier erythrocytes (the encapsulation yield) is about 30%. In such instances, about 40% to about 60% of the starting erythrocytes were recovered.

One example of a predrug that is suitable for use with the present invention is d-21P. As with the polypeptide, the percentage of d-21P that can be encapsulated into carrier erythrocytes (the encapsulation yield) is about 30%. Again, about 40% to about 60% of the starting erythrocytes were recovered.

In the case in which it is desired to obtain macrophage-targeted carrier RBCs, the following steps may be employed. First, the reconstituted, (i.e., loaded), RBCs are washed with saline containing 1 mM $ZnCl_2$. The $ZnCl_2$ acts as a clustering agent by inducing clustering of the transmembrane proteins of the RBCs. Next, a solution containing 1 mM bissulfosuccinimidilsuberate ($BS^3$) is added. $BS^3$ acts as a cross-linking agent which causes protein clusters induced by $ZnCl_2$ to become irreversible even upon $ZnCl_2$ removal. The incubation with $BS^3$ is allowed to proceed for about 15 minutes. The resulting cross-linked erythrocytes are then washed with saline and concentrated by conventional methods.

EQUIVALENTS

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for encapsulating at least one biologically active agent within an erythrocyte sample comprising:
   a) providing a volume of erythrocytes;
   b) lysing the erythrocytes;
   c) concentrating the lysed erythrocytes;
   d) contacting the concentrated, lysed erythrocytes with one or more biologically active agents; and
   e) sealing the lysed erythrocytes to thereby encapsulate the biologically active agents within at least a portion of the erythrocytes.

2. The method of claim 1, wherein the erythrocytes are swollen prior to the lysing step.

3. The method of claim 1, wherein some of the erythrocytes are fully lysed.

4. The method of claim 1, wherein the erythrocytes are lysed by adding a volume of at least one hypotonic solution to the volume of erythrocytes.

5. The method of claim 4, wherein in step (c) the lysed erythrocytes are concentrated so that the volume of the solution containing the erythrocytes is about 0.1 to about 0.067 that of the volume of the solution before concentrating.

6. The method of claim 4, wherein in step (c) the lysed erythrocytes are concentrated using a hemofilter.

7. The method of claim 1, wherein the erythrocytes are concentrated using a hemofilter.

8. A method for encapsulating at least one biologically active agent within an erythrocyte sample comprising:
   a) exposing the erythrocytes to a first hypotonic solution to cause the erythrocytes to become swollen;
   b) exposing the erythrocytes to a second hypotonic solution to cause the erythrocytes to become lysed;
   c) concentrating the erythrocytes;
   d) contacting the concentrated, lysed erythrocytes with one or more biologically active agents; and
   e) exposing the lysed erythrocytes to a sealing solution to thereby encapsulate at least some of the biologically active agents within at least a portion of the erythrocytes.

9. The method of claim 8, wherein the first hypotonic solution comprises about 6 volumes of physiological saline and about 4.5 volumes of distilled, sterile $H_2O$.

10. The method of claim 8, wherein the second hypotonic solution comprises about 6 volumes of physiological saline and about 8 volumes of distilled, sterile $H_2O$.

11. The method of claim 8, wherein the erythrocytes are concentrated using a hemofilter.

12. The method of claim 8, wherein the one or more biologically active agents are selected from the group consisting of peptides, oligopeptides, polypeptides, proteins, hormones, corticosteroids, glucocorticoids, non-steroidal anti-inflammatory agents, glutathione, cytokines, toxins, oligonucleotides, nucleic acids, and nucleoside analogs.

13. The method of claim 8, wherein the one or more biologically active agents are selected from the group consisting of dexamethasone-21-phosphate, prednisolone-21-phosphate, 6-mercaptopurine, azidothymidine, dideoxycytosine, and dideoxyinosine.

14. The method of claim 8, wherein the sealing solution comprises a Phosphate-Inosine-Glucose-Pyruvate-Adenine solution.

15. The method of claim 14, wherein about 5 ml of sealing solution is used for each aliquot of about 70–80 ml of lysed erythrocytes.

16. The method of claim 15 wherein, while contacted with the sealing solution, the lysed erythrocytes are incubated at about 37° C. for about 30 minutes.

17. The method of claim 8, wherein some of the erythrocytes are fully lysed after contacting with the second hypotonic solution.

18. The method of claim 8, wherein the erythrocytes are exposed to the first and second hypotonic solutions by suspending the erythrocytes in the first and second hypotonic solutions.

19. A method for encapsulating at least one biologically active agent within an erythrocyte sample comprising:
   a) providing a sample of erythrocytes from a donor;
   b) suspending the erythrocytes in a first hypotonic solution to cause the erythrocytes to become swollen, the erythrocytes being present in the first hypotonic solution at a concentration of about 0.04 to about 0.05 ml erythrocytes per ml solution;
   c) suspending the erythrocytes in a second hypotonic solution having an osmolality that is about 30 to about 60 mOsm less than that of the first solution, to cause the erythrocytes to become lysed;
   d) concentrating the resulting suspension so that the resulting volume of erythrocytes is about 0.01 to about 0.067 times that of the volume of the first hypotonic solution;
   e) contacting the concentrated lysed, erythrocytes with one or more biologically active agents; and
   f) exposing the lysed erythrocytes to a sealing solution to thereby encapsulate at least some of the biologically active agents within at least a portion of the erythrocytes, the sealing solution comprising a concentrated saline solution having a concentration such that the osmolality of the resulting solution is brought to about 1.9 to about 2.1 times that of the first hypotonic solution.

20. The method of claim 19, wherein the erythrocyte suspension is concentrated using a hemofilter.

21. The method of claim 19, wherein the one or more biologically active agents are selected from the group consisting of peptides, oligopeptides, polypeptides, proteins, hormones, corticosteroids, glucocorticoids, non-steroidal anti-inflammatory agents, glutathione, cytokines, toxins, oligonucleotides, nucleic acids, and nucleoside analogs.

22. The method of claim 19, wherein the one or more biologically active agents are selected from the group consisting of dexamethasone-21-phosphate, prednisolone-21-phosphate, 6-mercaptopurine, azidothymidine, dideoxycytosine, and dideoxyinosine.

23. The method of claim 19, which further comprises the step of treating the erythrocytes encapsulating at least one biologically active agent with a targeting agent such that the treated erythrocytes are preferentially directed to a specific tissue or cell type.

24. The method of claim 23, wherein the targeting agent comprises $ZnCl_2$ and bissulfosuccinimidilsuberate, and the treated erythrocytes are preferentially directed to macrophages.

* * * * *